US009782957B2

(12) United States Patent
Reinprecht et al.

(10) Patent No.: US 9,782,957 B2
(45) Date of Patent: Oct. 10, 2017

(54) MEDICAL DEVICE FILMS

(75) Inventors: Jon T. Reinprecht, Watertown, CT (US); Seth Gleiman, Guilford, CT (US); Amin Elachchabi, Hamden, CT (US); Ryan Witherell, Glastonbury, CT (US); Joshua Stopek, Guilford, CT (US); Garrett Ebersole, New Haven, CT (US)

(73) Assignee: Covidien LP, Mansfield, MA (US)

( * ) Notice: Subject to any disclaimer, the term of this patent is extended or adjusted under 35 U.S.C. 154(b) by 1031 days.

(21) Appl. No.: 13/589,222

(22) Filed: Aug. 20, 2012

(65) Prior Publication Data

US 2013/0053765 A1 Feb. 28, 2013

Related U.S. Application Data

(60) Provisional application No. 61/526,885, filed on Aug. 24, 2011.

(51) Int. Cl.
| A61M 5/00 | (2006.01) |
| B05D 3/12 | (2006.01) |
| B32B 27/36 | (2006.01) |
| A61L 27/54 | (2006.01) |
| B29C 47/00 | (2006.01) |
| B32B 7/12 | (2006.01) |
| B32B 9/02 | (2006.01) |
| B32B 23/00 | (2006.01) |
| B32B 27/08 | (2006.01) |

(52) U.S. Cl.
CPC .............. *B32B 27/36* (2013.01); *A61L 27/54* (2013.01); *B29C 47/0021* (2013.01); *B32B 7/12* (2013.01); *B32B 9/02* (2013.01); *B32B 23/00* (2013.01); *B32B 27/08* (2013.01); *A61L 2300/402* (2013.01); *A61L 2420/08* (2013.01); *B32B 2250/244* (2013.01); *B32B 2255/10* (2013.01); *B32B 2255/26* (2013.01); *B32B 2307/7163* (2013.01); *B32B 2535/00* (2013.01)

(58) Field of Classification Search
None
See application file for complete search history.

(56) References Cited

U.S. PATENT DOCUMENTS

| 3,054,406 A | 9/1962 | Usher |
| 3,887,699 A | 6/1975 | Yolles |
| 4,767,628 A | 8/1988 | Hutchinson |
| 4,931,546 A | 6/1990 | Tardy et al. |
| 5,147,374 A | 9/1992 | Fernandez |
| 5,195,542 A | 3/1993 | Gazielly et al. |
| 5,254,133 A | 10/1993 | Seid |
| 5,258,000 A | 11/1993 | Gianturco |
| 5,368,602 A | 11/1994 | de la Torre |
| 5,370,650 A | 12/1994 | Tovey et al. |
| 5,571,525 A * | 11/1996 | Roorda et al. ................ 424/426 |
| 5,593,441 A | 1/1997 | Lichtenstein et al. |
| 5,634,931 A | 6/1997 | Kugel |
| 5,695,525 A | 12/1997 | Mulhauser et al. |
| 5,702,416 A | 12/1997 | Kieturakis et al. |
| 5,711,960 A | 1/1998 | Shikinami |
| 5,743,917 A | 4/1998 | Saxon |
| 5,766,246 A | 6/1998 | Mulhauser et al. |
| 5,769,864 A | 6/1998 | Kugel |
| 5,916,225 A | 6/1999 | Kugel |
| 5,922,026 A | 7/1999 | Chin |
| 6,042,534 A | 3/2000 | Gellman et al. |
| 6,120,539 A | 9/2000 | Eldridge et al. |
| 6,162,962 A | 12/2000 | Hinsch et al. |
| 6,171,318 B1 | 1/2001 | Kugel et al. |
| 6,180,848 B1 | 1/2001 | Flament et al. |
| 6,210,439 B1 | 4/2001 | Firmin et al. |
| 6,214,020 B1 | 4/2001 | Mulhauser et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,270,792 B1 | 8/2001 | Guillemet et al. |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,319,264 B1 | 11/2001 | Törmälä |
| 6,383,201 B1 | 5/2002 | Dong |
| 6,425,924 B1 | 7/2002 | Rousseau |
| 6,447,551 B1 | 9/2002 | Goldmann |
| 6,485,503 B2 | 11/2002 | Jacobs et al. |
| 6,500,777 B1 | 12/2002 | Wiseman et al. |
| 6,596,002 B2 | 7/2003 | Therin et al. |
| 6,610,006 B1 | 8/2003 | Amid et al. |
| 6,616,685 B2 | 9/2003 | Rousseau |
| 6,645,226 B1 | 11/2003 | Jacobs et al. |
| 6,669,735 B1 | 12/2003 | Pelissier |
| 6,712,859 B2 | 3/2004 | Rousseau et al. |
| 6,736,823 B2 | 5/2004 | Darois et al. |
| 6,736,854 B2 | 5/2004 | Vadurro et al. |
| 6,755,868 B2 | 6/2004 | Rousseau |
| 6,790,213 B2 | 9/2004 | Cherok et al. |
| 6,800,082 B2 | 10/2004 | Rousseau |
| 6,872,227 B2 | 3/2005 | Sump et al. |
| 6,926,723 B1 | 8/2005 | Mulhauser et al. |
| 7,011,688 B2 | 3/2006 | Gryska et al. |
| 7,021,086 B2 | 4/2006 | Ory et al. |
| 7,041,868 B2 | 5/2006 | Greene et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,101,381 B2 | 9/2006 | Ford et al. |

(Continued)

FOREIGN PATENT DOCUMENTS

| EP | 2 016 956 A2 | 1/2009 |
| EP | 2 404 571 A1 | 1/2012 |

(Continued)

*Primary Examiner* — Adam C Milligan

(57) ABSTRACT

Medical devices described herein include a melt-pressed film having first and second diffusion barrier layers disposed thereon. The melt-pressed film and the barrier layers comprise bioabsorbable copolymers. In a further aspect, a therapeutic agent, such as an analgesic is included in the medical device.

13 Claims, 8 Drawing Sheets

(56) References Cited

U.S. PATENT DOCUMENTS

| | | |
|---|---|---|
| 7,156,858 B2 | 1/2007 | Schuldt-Hempe et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,404,819 B1 | 7/2008 | Darios et al. |
| 7,556,598 B2 | 7/2009 | Rao |
| 7,594,921 B2 | 9/2009 | Browning |
| 7,785,334 B2 | 8/2010 | Ford et al. |
| 7,806,905 B2 | 10/2010 | Ford et al. |
| 8,123,817 B2 | 2/2012 | Intoccia et al. |
| 2002/0099344 A1 | 7/2002 | Hessel et al. |
| 2002/0131988 A1 | 9/2002 | Foster et al. |
| 2004/0098118 A1 | 5/2004 | Granada et al. |
| 2004/0215219 A1 | 10/2004 | Eldridge et al. |
| 2004/0224007 A1 | 11/2004 | Zhang |
| 2005/0240261 A1 | 10/2005 | Rakos et al. |
| 2005/0244455 A1 | 11/2005 | Greenawalt |
| 2005/0261782 A1 | 11/2005 | Hoganson |
| 2006/0034887 A1 | 2/2006 | Pelissier |
| 2006/0116696 A1 | 6/2006 | Odermatt et al. |
| 2006/0121078 A1 | 6/2006 | Trogolo et al. |
| 2006/0188546 A1 | 8/2006 | Giroux |
| 2006/0224038 A1 | 10/2006 | Rao |
| 2006/0253203 A1 | 11/2006 | Alvarado |
| 2007/0129736 A1 | 6/2007 | Solecki |
| 2007/0198040 A1 | 8/2007 | Buevich et al. |
| 2007/0244548 A1 | 10/2007 | Myers et al. |
| 2007/0260268 A1 | 11/2007 | Bartee et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0147200 A1 | 6/2008 | Rousseau et al. |
| 2008/0172071 A1 | 7/2008 | Barker |
| 2008/0199506 A1 | 8/2008 | Horres et al. |
| 2008/0255593 A1 | 10/2008 | St-Germain |
| 2009/0036996 A1 | 2/2009 | Roeber |
| 2009/0069826 A1 | 3/2009 | Walther et al. |
| 2009/0082792 A1 | 3/2009 | Koyfman et al. |
| 2009/0105526 A1 | 4/2009 | Piroli Torelli et al. |
| 2009/0125107 A1 | 5/2009 | Maxwell |
| 2009/0142385 A1 | 6/2009 | Gross et al. |
| 2009/0163936 A1 | 6/2009 | Yang et al. |
| 2009/0171377 A1 | 7/2009 | Intoccia et al. |
| 2009/0187197 A1 | 7/2009 | Roeber et al. |
| 2009/0192530 A1 | 7/2009 | Adzich et al. |
| 2009/0198260 A1 | 8/2009 | Ford et al. |
| 2009/0270999 A1 | 10/2009 | Brown |
| 2009/0276057 A1 | 11/2009 | Trabucco et al. |
| 2009/0326676 A1 | 12/2009 | Dupic et al. |
| 2010/0003308 A1 | 1/2010 | Tapolsky et al. |
| 2010/0087840 A1* | 4/2010 | Ebersole et al. .............. 606/151 |
| 2010/0089409 A1 | 4/2010 | Bertagnoli |
| 2010/0160375 A1 | 6/2010 | King |
| 2010/0239635 A1* | 9/2010 | McClain et al. .............. 424/423 |
| 2010/0286716 A1 | 11/2010 | Ford et al. |
| 2011/0144667 A1 | 6/2011 | Horton et al. |
| 2011/0265283 A1 | 11/2011 | Duncan |

FOREIGN PATENT DOCUMENTS

| | | |
|---|---|---|
| FR | 2 601 371 A1 | 1/1988 |
| FR | 2 857 851 A1 | 1/2005 |
| WO | WO 93/11805 A1 | 6/1993 |
| WO | WO 99/51163 A1 | 10/1999 |
| WO | WO 02/34304 A1 | 5/2002 |
| WO | WO 03/007847 A1 | 1/2003 |
| WO | WO 2006/020922 A2 | 2/2006 |
| WO | WO 2006/036967 A1 | 4/2006 |
| WO | WO 2006/102374 A2 | 9/2006 |
| WO | WO 2008/127411 A1 | 10/2008 |
| WO | WO 2009/075786 A1 | 6/2009 |
| WO | WO 2010/093333 A1 | 8/2010 |

\* cited by examiner

| Zone | Disciption | Temperature |
|------|------------|-------------|
| 1 | Polymer Feed/Conveying | 130 |
| 2 | Kneading | 135 |
| 3 | Bupivacaine Feed | 144 |
| 4 | Kneading | 133 |
| 5 | Distributive Mixing | 133 |
| 6 | Vent | 133 |
| 7 | Pumping | 133 |
| 8 | Die | 155 |

| Trial | Material #1 | Material #2 | Material #1 (g/min) | Material #2 (g/min) | Material #2 Conc. % |
|---|---|---|---|---|---|
| 1 | Polymer | Bupivacaine | 16 | 0 | 0 |
| 2 | Polymer | Bupivacaine | 11.7 | 5 | 30 |
| 3 | Polymer | Bupivacaine | 8.3 | 8.3 | 50 |
| 4 | Polymer | Bupivacaine | 10 | 6.7 | 40 |
| 5 | Polymer | Bupivacaine | 11.7 | 5 | 30 |

| ZONE 1 | ZONE 2 | ZONE 3 | ZONE 4 | ZONE 5 | ZONE 6 | ZONE 7 | ZONE 8 |
|---|---|---|---|---|---|---|---|
| 165 | 165 | 185 | 165 | 165 | 165 | 170 | 185 |

MEDICAL DEVICE FILMS

CROSS-REFERENCE

This application claims the priority to and benefit of U.S. Provisional Patent Application Ser. No. 61/526,885 filed on Aug. 24, 2011the entire content of which is hereby incorporated by reference.

BACKGROUND

Technical Field

The present disclosure relates to medical devices for drug delivery. In embodiments, the medical device includes a melt-pressed film and at least one diffusion barrier layer.

Description of Related Art

Current technology related to making medical devices, such as films, includes extrusion, film casting, spraying, and the like. In particular, for drug delivery applications, spraying films is desirable for several reasons including precision in application of materials and the ability to combine traditionally incompatible systems. However, spraying has disadvantages including increased processing time and the use of volatile solvents.

Improvements in the field, including use of less solvent and improving processing and manufacturing time are desired.

SUMMARY

Disclosed herein is a medical device comprising a first spray coated diffusion barrier layer, a second spray coated diffusion barrier layer, and a melt-pressed film disposed therebetween. In some embodiments, the melt-pressed film comprises a material selected from the group consisting of homopolymers and copolymers of lactide; glycolide; epsilon-caprolactone, p-dioxanone; trimethylene carbonate; alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one; 1,5-dioxepan-2-one; 6,6-dimethyl-1,4-dioxan-2-one; 2,5-diketomorpholine; pivalolactone; α, α diethylpropiolactone; ethylene carbonate; ethylene oxalate; 3-methyl-1,4-dioxane-2,5-dione; 3,3-diethyl-1,4-dioxan-2,5-dione; and 6,8-dioxabicycloctane-7-one. In one particular embodiment, the melt-pressed film comprises glycolide, trimethylene carbonate, epsilon-caprolactone, and lactide. Optionally, the melt-pressed film comprises a random copolymer. The melt-pressed film may be from about 1 millimeter thick to about 10 millimeters thick.

The melt-pressed film may further comprise a therapeutic agent selected from the group consisting of anti-adhesives, antimicrobials, analgesics, and, anesthetics. For example, the therapeutic agent may include bupivacaine. The therapeutic agent may be at a concentration of from about 30% to about 50% of the melt-pressed film.

The first or the second diffusion barrier layer comprises a biodegradable material. In one embodiment, the first or second diffusion barrier layer comprises glycolide and caprolactone. The thickness of the barrier layers may be from about 1 micron to about 50 microns thick. The first or second diffusion barrier layer may be applied via a spray coating process.

Methods for making medical devices are also disclosed herein. The method includes admixing a drug and a polymer, extruding the drug and polymer to form an extrudate, converting the extrudate into a film, and; coating at least a first surface of the film with a diffusion barrier layer. The drug and the polymer may be admixed in an extruder. Further, the diffusion barrier layer may be spray coated onto the first surface of the film.

An alternate embodiment of a medical device is disclosed herein in which the medical device includes a copolymer film including about 69% glycolide, about 7% trimethylene carbonate, about 17% caprolactone, about 7% lactide; wherein the copolymer film is disposed between a first and second barrier layer; and, at least one of the first and second barrier layers includes about 90% caprolactone and about 10% glycolide. The copolymer film may further include a therapeutic agent at a concentration of from about 40% by weight to about 50% by weight.

BRIEF DESCRIPTION OF THE DRAWINGS

Various embodiments of the present disclosure will be discussed in more detail below in conjunction with selected embodiments and the appended drawings wherein.

DETAILED DESCRIPTION

Figure 1:
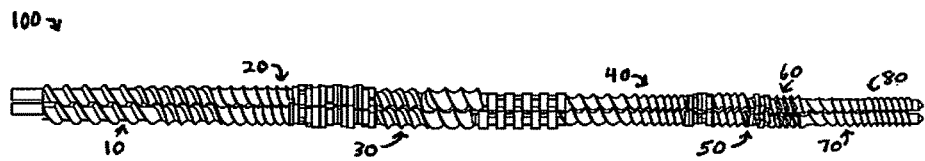
FIG. 1 illustrates a twin screw in accordance with the present disclosure.

Medical devices in accordance with the present disclosure include a melt-pressed film having first and second diffusion barrier layers. The diffusion barrier layers are spray coated on a first surface and a second surface of the film, sandwiching the melt-pressed film therebetween. The diffusion barrier layers may comprise materials suitable for drug delivery, including biodegradable materials. In certain embodiments, the melt-pressed film comprises biodegradable materials. Medical devices disclosed herein are suitable for drug delivery, more specifically, the melt-pressed film and/or the diffusion barrier layers may comprise therapeutic agents. The term "melt-pressed film" as used herein includes a polymer film which has been pressed from the molten state or at a temperature around the Melting Temperature (Tm) of the polymer. Methods for pressing films, which will be later described, include use of rollers, a carver press, or an extruder.

The medical devices described herein may be manufactured from biodegradable and non-biodegradable materials. As used herein, the term "biodegradable" includes both bioabsorbable and bioresorbable materials. By biodegradable, it is meant that the materials decompose, or lose structural integrity under body conditions (e.g., enzymatic degradation, hydrolysis) or are broken down (physically or chemically) under physiologic conditions in the body (e.g., dissolution) such that the degradation products are excretable or absorbable by the body.

Some non-limiting examples of biodegradable materials which may be used to form the medical devices include polymers such as aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as such as poly (bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

More specifically, aliphatic polyesters include, but are not limited to, homopolymers and copolymers of lactide (including lactic acid, D-,L- and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl- 1,4-dioxan-2-one; 2,5-diketomorpholine; pivalolactone; α, α diethylpropiolactone; ethylene carbonate; ethylene oxalate; 3-methyl-1,4-dioxane-2,5-dione; 3,3-diethyl-1,4-dioxan-2, 5-dione; 6,8-dioxabicycloctane-7-one; and polymer blends and copolymers thereof.

In certain embodiments, the melt-pressed films comprise copolymers of about 69% glycolide, about 7% trimethylene carbonate, about 17% ε-caprolactone and about 7% lactide. The diffusion layers comprise copolymers of about 90% ε-caprolactone and about 10% glycolide.

Other suitable biodegradable polymers for use in the present disclosure include, but are not limited to, poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses".

In certain embodiments, it may be desirable to have a non-biodegradable melt-pressed film for permanent tissue support. Suitable non-biodegradable materials include: polyolefins such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof. Mixtures and blends of such biocompatible polymeric or copolymeric materials may also be useful.

The medical devices described herein may further include a therapeutic agent. The term "therapeutic agent," as used herein, is used in its broadest sense and includes any substance or mixture of substances that provides a beneficial, therapeutic, pharmacological, and/or prophylactic effect. The agent may be a drug which provides a pharmacological effect.

The term "drug" is meant to include any agent capable of rendering a therapeutic effect, such as, anti-adhesives, antimicrobials, analgesics, antipyretics, anesthetics (e.g., local and systemic), antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of agents may be used.

Other therapeutic agents, which may be included as a drug include: anti-fertility agents; parasympathomimetic agents; psychotherapeutic agents; tranquilizers; decongestants; sedative hypnotics; sulfonamides; sympathomimetic agents; vaccines; vitamins; antimalarials; anti-migraine agents; antiparkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; and immunological agents.

Other examples of suitable agents, which may be included in the medical devices described herein include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (e.g., IL-2, IL-3, IL-4, IL-6); interferons (e.g., β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids such as antisense molecules, DNA, RNA, and RNAi; oligonucleotides; polynucleotides; and ribozymes.

Some specific non-limiting examples of water-soluble drugs that may be used in the present disclosure include, lidocaine, bupivacaine, tetracaine, procaine, dibucaine, sirolimus, taxol, chlorhexidine, polyhexamethylene, thiamylal sodium, thiopental sodium, ketamine, flurazepam, amobarbital sodium, phenobarbital, bromovalerylurea, chloral hydrate, phenytoin, ethotoin, trimethadione, primidone, ethosuximide, carbamazepine, valproate, acetaminophen, phenacetin, aspirin, sodium salicylate, aminopyrine, antipyrine, sulpyrine, mepirizole, tiaramide, perixazole, diclofenac, anfenac, buprenorphine, butorphanol, eptazocine, dimenhydrinate, difenidol, dl-isoprenaline, chlorpromazine, levomepromazine, thioridazine, fluphenazine, thiothixene, flupenthixol, floropipamide, moperone, carpipramine, clocapramine, imipramine, desipramine, maprotiline, chlordiazepoxide, clorazepate, meprobamate, hydroxyzine, saflazine, ethyl aminobenzoate, chlorphenesin carbamate, methocarbamol, acetylcholine, neostigmine, atropine, scopolamine, papaverine, biperiden, trihexyphenidyl, amantadine, piroheptine, profenamine, levodopa, mazaticol, diphenhydramine, carbinoxamine, chlorpheniramine, clemastine, aminophylline, choline, theophylline, caffeine, sodium benzoate, isoproterenol, dopamine, dobutamine, propranolol, alprenolol, bupranolol, timolol, metoprolol, procainamide, quinidine, ajmaline, verapamil, aprindine, hydrochlorothiazide, acetazolamide, isosorbide, ethacrynic acid, captopril, enalapril, delapril, alacepril, hydralazine, hexamethonium, clonidine, bunitrolol, guanethidine, bethanidine, phenylephrine, methoxamine, diltiazem, nicorandil, nicametate, nicotinic-alcohol tartrate, tolazoline, nicardipine, ifenprodil, piperidinocarbamate, cinepazide, thiapride, dimorpholamine, levallorphan, naloxone, hydrocortisone, dexamethasone, prednisolone, norethisterone, clomiphene, tetracycline, methyl salicylate, isothipendyl, crotamiton, salicylic acid, nystatin, econazole, cloconazole, vitamin $B_1$, cycothiamine, vitamin $B_2$, vitamin $B_3$, vitamin $B_5$, vitamin $B_6$, vitamin $B_7$, vitamin $B_9$, vitamin $B_{12}$, vitamin C, nicotinic acid, folic acid, nicotinamide, calcium pantothenate, pantothenol, panthetin, biotin, ascorbic acid, tranexamic acid, ethamsylate, protamine, colchicine, allopurinol, tolazamide, glymidine, glybuzole, metoformin, buformin, orotic acid, azathioprine, lactulose, nitrogen mustard, cyclophophamide, thio-TEPA, nimustine, thioinosine, fluorouracil, tegafur, vinblastine, vincristine, vindesine, mitomycin C, daunorubicin, aclarubicin, procarbazine, cisplatin, methotrexate, benzylpenicillin, amoxicillin, penicillin, oxycillin, methicillin, carbenicillin, ampicillin, cefalexin, cefazolin, erythromycin, kitasamycin, chloramphenicol, thiamphenicol, minocycline, lincomycin, clindamycin, streptomycin, kanamycin, fradiomycin, gentamycin, spectinomycin, neomycin, vanomycin, tetracycline, ciprofloxacin, sulfanilic acid, cycloserine, sulfisomidine, isoniazid, ethambutol, acyclovir, gancyclovir, vidabarine, azidothymidine, dideoxyinosine, dideoxycytosine, morphine, codeine, oxycodone, hydrocodone, cocaine, pethidine, fentanyl, polymeric forms of any of the above drugs and any combinations thereof. Although the above therapeutic agents have been provided for the purposes of illustration, it should be understood that the present disclosure is not so limited. In particular, although certain therapeutic agents are specifically referred to above, the present disclosure should be understood to include analogues, derivatives and conjugates of such agents. For example, a water-soluble drug may not need to be converted to a salt form, e.g., tetracycline hydrochloride.

In particular embodiments, the therapeutic agent may include an anesthetic, e.g., bupivacaine hydrochloride, lidocaine, benzocaine, and the like, within melt-pressed film. Alternatively, a therapeutic agent may be contained solely on a surface of the melt-pressed film. Additionally, therapeutic agent may also be disposed within, on, or between the first and/or second diffusion barrier layers. The therapeutic agent contained within or on the melt-pressed film may be the same as or different than any therapeutic agent found within or thereon a diffusion barrier layer. Combinations of the above are also within the scope of the present disclosure.

In certain embodiments, the melt-pressed film comprises a copolymer of about 69% glycolide, about 7% trimethylene carbonate, about 17% ε-caprolactone and about 7% lactide in combination with a therapeutic agent, such as bupivacaine. The bupivacaine is at a concentration of from about 20% to about 80%, and in particular embodiments, from about 40% to about 50% of the total concentration of the melt-pressed film. More specifically, the bupivacaine is disposed within the film and additionally is present on the surface of the film.

Melt-pressed films of the present disclosure have a high therapeutic agent concentration. In particular embodiments, as the therapeutic agent is from about 40 to about 50% of the total concentration of the film, not all processing methods are suitable for addition of therapeutic agents in such high concentrations. Further, as the concentration of the therapeutic agent increases, certain manufacturing processes require additional time and solvents. As such, time and cost-effective methods for attaining a higher concentration of a melt-pressed film, include processing operations that involve high shearing.

One particular method for making the melt-pressed film include admixing a therapeutic agent, e.g., a drug and the copolymer in an extruder, e.g., a twin screw extruder, then gathering the extrudate. The twin screw extruder may additionally include a one strand pelletizing die which can convert the extrudate into pellets and the pellets are heated and pressed into a film, using, for example, a Carver press.

In one particular embodiment, an 18 mm high performance (HP) twin screw extruder is utilized to mix a copolymer of glycolide, trimethylene carbonate, caprolactone, and lactide in combination with a therapeutic agent such as bupivacaine. In particular, FIG. 1 illustrates a twin screw 100 having high shear elements which may be used in combination with a barrel having low barrel temperatures for processing a copolymer in combination with bupivacaine. The copolymer flows from left to right and the feed section is on the left. In one particular embodiment, a Leistritz ZSE-18 co-rotating twin screw extruder system can be utilized; the details are which are included in FIGS. 1A-1I, and described hereinbelow.

Figure 1A:
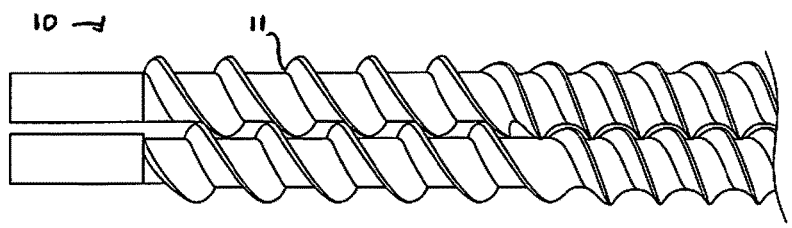
FIGS. 1A-1I illustrate various sections of the twin screw of FIG. 1 in accordance with the present disclosure.
Figure 1B:
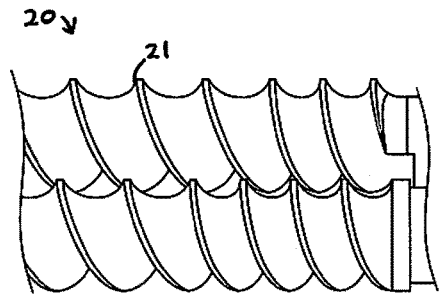

In more detail, FIG. 1A illustrates a feed section 10 of the twin screw extruder 100 of FIG. 1. The feed zone 10 includes wide flights 11 and a narrow pitch which allows fast transport of polymer pellets out of the feed section 10. As the copolymer pellets move out of the feed section 10 and into the next screw section 20 (FIG. 1B), the pellets absorb more heat. This section 20 includes tighter flighted elements 21, and the copolymer stays in this zone for a longer period of time, softening the copolymers and initiating the melt.

Figure 1C:
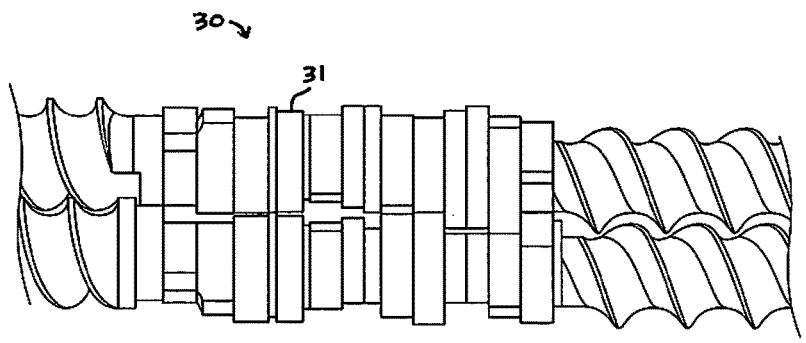
Figure 1D:
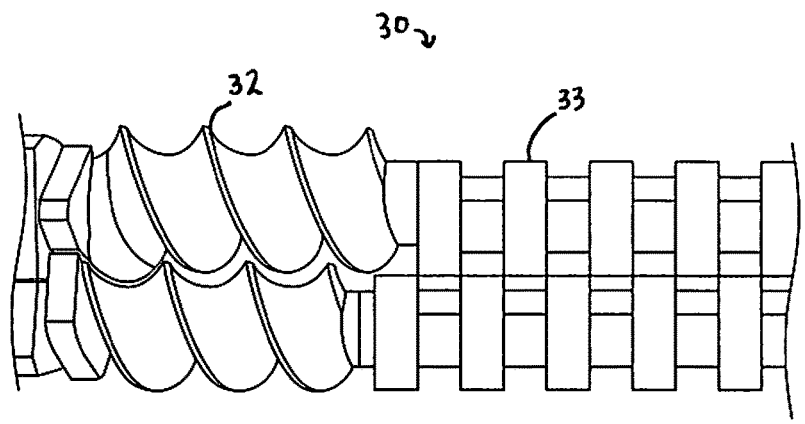
Figure 1E:
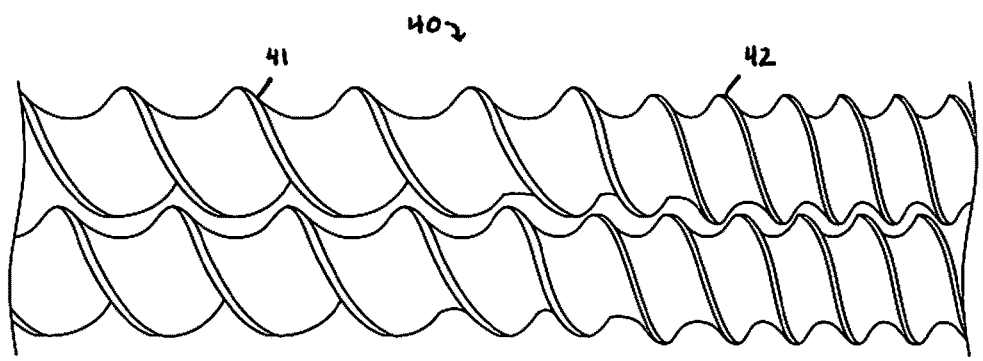

Next, the copolymers enter Zone 2 (30), illustrated in FIGS. 1C and 1D. Zone 2 (30) includes a first set of kneading blocks 31 comprised of two 15 mm elements with a 30° offset. The copolymer pellets enter this section and are melted by the shear forces present during screw rotation. The slight forward conveyance due to the block indexing is significantly less than standard flighted elements. Zone 2 (30) includes higher pressure and extended residence time, promoting copolymer melting.

After kneading, the molten copolymer is conveyed by a short set of flighted elements 32 to a longer set of kneading blocks 33 with a 90° offset, shown in FIG. 1D. In this section, the copolymer has an increased residence time, thoroughly melting the copolymer by the time the copolymer exits Zone 2 (30). Further, Zone 2 (30) serves as a melt seal, eliminating upstream flow of copolymer of any additive.

As the copolymer is pushed out of Zone 2 (30), it enters a low pressure zone, Zone 3 (40) (FIG. 1E), having flighted elements 41. In Zone 3 (40), the therapeutic agent is added to the molten copolymer. The therapeutic agent may be added to Zone 3 (40) utilizing a side stuffer configuration (not shown). In Zone 3 (40), the conveying elements 42 mix the therapeutic agent and molten copolymer and carry them into Zone 4 (50).

Figure 1F:
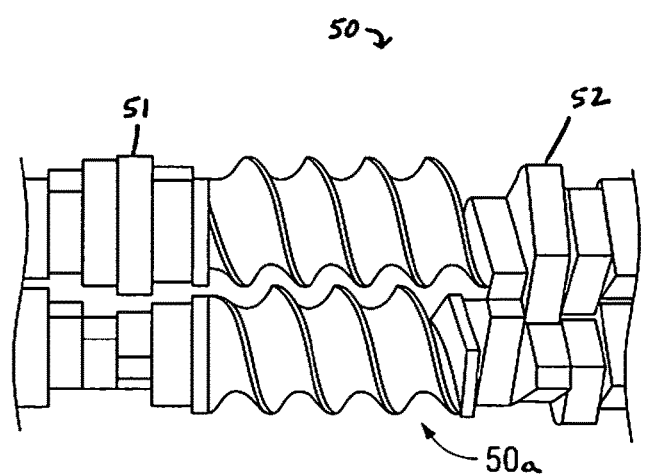
Figure 1G:
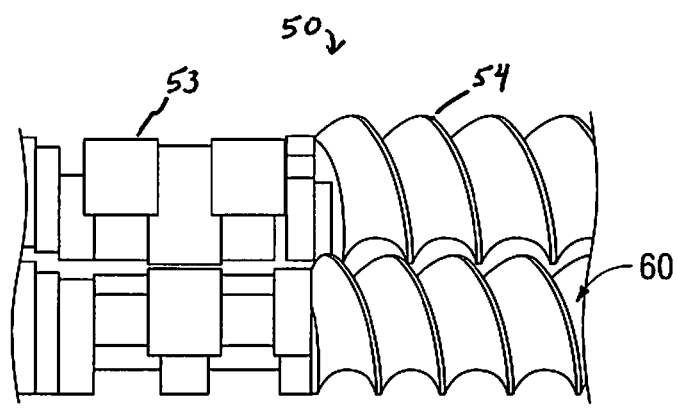

Zone 4 (50), illustrated in FIG. 1F, includes 30° offset kneading elements 51, which create higher levels of shear to crush and disperse large agglomerates of the therapeutic agent powder and initiate the compounding of the therapeutic agent into the copolymer. A short conveying section 50a maintains forward pumping and moves the copolymer/therapeutic agent mixture into the next set of kneading blocks 52. This second set of kneading blocks 52 has a 60° offset, exposing the copolymer to more shear as the residence time increases. The copolymer/therapeutic agent mixture then enters another section having 90° offset wide kneading blocks 53, illustrated in FIG. 1G. This zone also includes a high residence time. Additionally, to maintain forward movement, a small section of flighted element 54 is present.

Figure 1H:
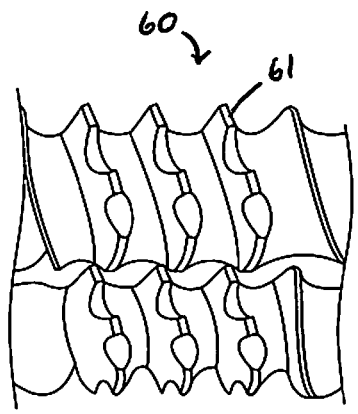

The copolymer/therapeutic agent mixture is then moved into Zone 5 (60), illustrated in FIG. 1H. Zone 5 (60) includes the last mixing operation of the twin screw. A set of highly distributive melting elements 61 homogenize and mixture.

Figure 1I:
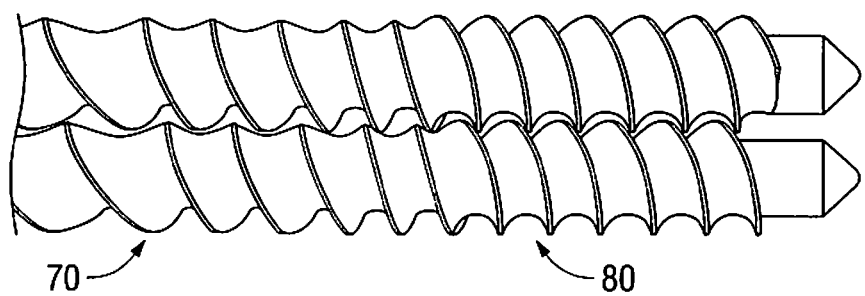

Lastly, Zones 6 and 7, shown in FIG. 1I, include a low pressure, wide flight element 70, followed by a compression and pumping section 80. Optionally, vacuum may be applied in the low pressure region to pull volatiles, moisture, reactants, or unwanted byproducts from the melt stream. Additionally, Zone 8 (not shown) includes a strand die, which the extrudate exits.

Pellets of the copolymer mixture may be collected following extrusion through use of a pelletizing die. The pellets can then be reheated and melt-pressed into a film. Suitable methods for melt-pressing films are within the art and include but are not limited to a Carver press, extrusion and the like. Alternatively, the twin screw extruder may contain a die for pressing the molten polymer into films. In other embodiments, melt-pressed films may be created by pressing the film using rollers.

Once the melt-pressed film has been created, at least one diffusion barrier layer is applied to a surface thereof using methods including but not limited to dip coating, spray coating, solution casting and the like. In one particular embodiment, the diffusion barrier layers may be created through an ultrasonic spray coating technique. The diffusion barrier layer assists in modulating the release of the therapeutic agent from the medical device, and more specifically, from the melt-pressed film.

In particular, copolymer solutions which may be applied to melt-pressed films include biodegradable and non-biodegradable copolymers, copolymers and blends thereof. Suitable polymers include those disclosed herein. In one embodiment, a copolymer of about 10% ε-caprolactone and about 90% glycolide may be applied onto the melt-pressed films.

Polymer or copolymers are further combined with hydrophobic or hydrophilic solvents to create solutions suitable for application to the melt-pressed film, creating the diffusion barrier layers.

A copolymer solution may be passed through an ultrasonic spray nozzle to form the medical devices described herein. Ultrasonic sprayers include ultrasonic spray nozzles which may be used to generate vibrations leading to atomization of the solutions. Briefly, the sprayer body includes three principal sections: front horn, the atomizing section; rear horn, the rear section; and a section including a pair of disc-shaped piezoelectric transducers. Working in unison, these three elements provide means for creating the vibration required to atomize the solutions delivered to the nozzle surface. One or more solutions enter through a fitting on the rear horn, passes through a tube, and then a central axis of the front horn. Finally, the solution reaches the atomizing surface of the nozzle where atomization takes place. Piezoelectric transducers convert electrical energy provided by an external power source into high-frequency mechanical motion or vibration. The solution absorbs the underlying vibration energy and generates capillary waves. When the amplitude of the capillary waves exceeds a critical value, the waves collapse ejecting small droplets of the solutions.

The ultrasonic sprayer nozzle may include a variety of controls which may be adjusted to alter the characteristics of the films described herein. Some non-limiting examples include: vibration frequency, operational power; solution flow rates, nozzle speed, and length of movement of the nozzle. In forming the films described herein, the sprayer nozzle may vibrate at a frequency ranging from about 20 kHz to about 240 kHz, in some embodiments, a 120 kHz nozzle may be used. The nozzle may operate at a power ranging from about 2 to about 10 watts. In some embodiments, the sprayer nozzle may vibrate at a frequency of about 48 kHz and operate at a power of about 6 watts.

In certain embodiments, the ultrasonic spray nozzles may be movable. The nozzle may move a speed ranging from about 1 mm/sec to about 200 mm/sec. In other embodiments, the nozzle speed may range from about 50 mm/sec to about 150 mm/sec. In addition, the height of the movable nozzles may range from about 30 mm to about 60 mm from the inert substrate. As the nozzle moves across the substrate, creating the medical devices, each complete movement translating across the substrate is referred to as a 'pass'. For example, if the diffusion barrier layer is created by the nozzle passing across the substrates five times, the spray nozzle has taken five passes.

The flow rate of the solutions passed through the sprayer nozzle may vary within the range of about 0.1 mL/min to about 5 mL/min. In embodiments, the flow rate of the solutions may be within the range of about 0.5 mL/min and about 2.0 mL/min. It is envisioned that each of the sprayer controls may be individually adjusted for each of the different solutions being passed therethrough.

Figures 8, 9:
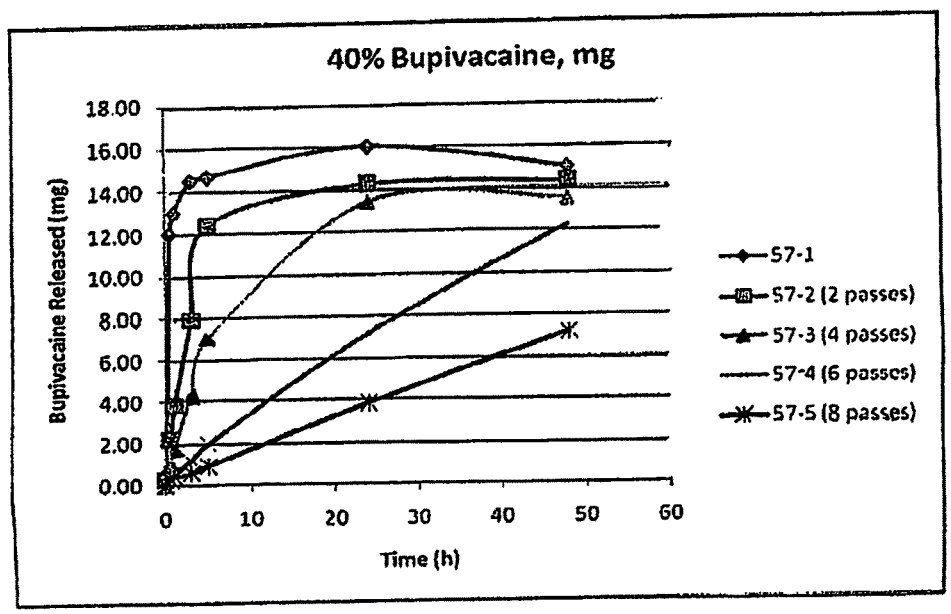
FIG. 8 is a chart illustrating five trial runs of polymer/therapeutic agent systems having various concentrations of bupivacaine.
FIG. 9 is a graph illustrating bupivacaine release vs. time for one embodiment of a medical device in accordance with the present disclosure.

The diffusion barrier layers may be of varying thicknesses to attain a desired release profile. In particular embodiments, the diffusion barrier layers are from about 0.01 micrometer to about 50 micrometers thick. More specifically, the diffusion barrier layers may be from about 0.1 micrometer to about 5 micrometers thick. As shown in FIGS. 8 and 9 (and later described), as the thickness of the diffusion barrier layers increase, the drug release profile changes. More specifically, for compositions according to the present disclosure, bupivacaine release changes from an exponential drug release profile to a linear drug release profile as the thickness of the diffusion barrier layers increase.

Further, the first diffusion barrier layer may be of a different thickness than a second diffusion barrier layer. For example, a thinner coating may be preferable on a surface of the medical device if a quicker or faster release rate is desirable. Alternatively, a thicker coating may be preferable on a surface of the medical device if a slower or longer release rate is desired. The medical device may have a thicker diffusion barrier layer on a first surface of the film and a thinner diffusion barrier layer on a second surface of the film, providing directional release of a therapeutic agent. It should be understood that coating thickness, film construction, materials selection, and other variables can contribute to the release rate of therapeutic agents from medical devices disclosed herein.

The diffusion barrier layers may comprise bioabsorbable polymers and in one particular embodiment, the diffusion barrier layers may comprise a copolymer of about 10% glycolide and about 90% lactide. It is envisioned that the first and second diffusion barrier layers may comprise the same copolymer composition, however it is within the scope of the disclosure that the first and second diffusion barrier layers may comprise different copolymers or a different copolymer composition.

The diffusion barrier layers may be sprayed directly onto a first surface and a second surface of the melt-pressed film. As described hereinabove, as the ultrasonic spray nozzle passes over the melt-pressed film, a diffusion barrier layer is created. The nozzle may continue to build up the diffusion barrier layer thickness by increasing the number of passes. In certain embodiments, the barrier layers may be of sufficient thickness to form films. The films may be continuous or discontinuous.

In other embodiments, the diffusion barrier layers may be sprayed onto an inert substrate or a release sheet. The diffusion barrier layer is combined with the melt-pressed film, and inert substrate or release sheet is removed from the diffusion barrier layer. In other embodiments, the inert substrate remains attached to the diffusion barrier layer and is incorporated as part of the medical device. Alternatively, the medical device may be combined with a film backing, such as collagen.

Figure 2:
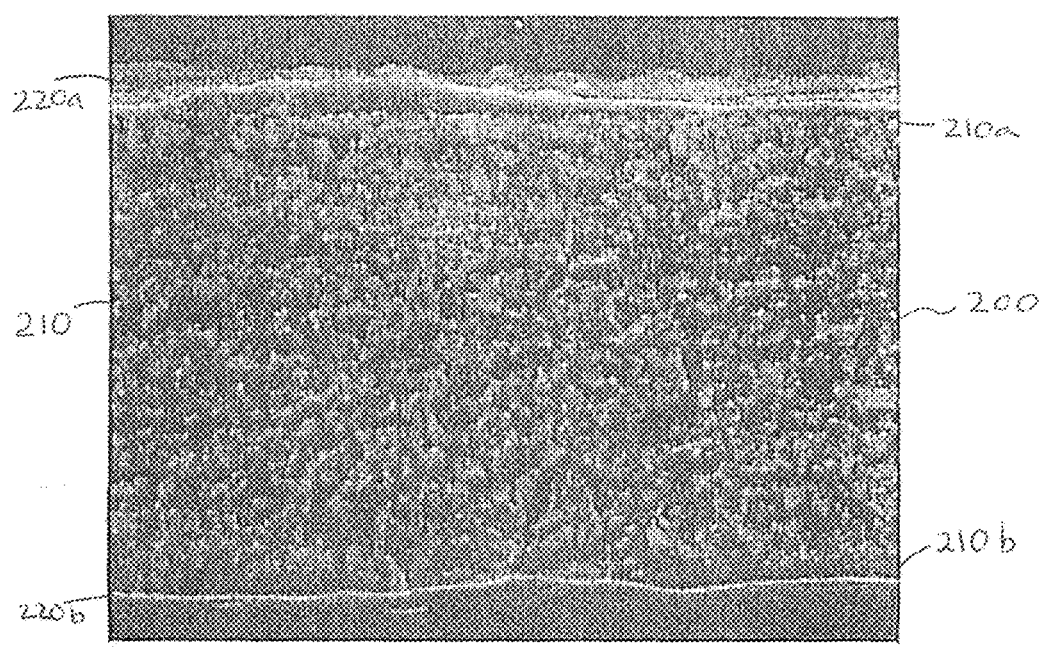
FIG. 2 is a Scanning Electron Microscope (SEM) image of a cross-sectional view of a medical device in accordance with the present disclosure.

Turning now to the figures, FIG. 2 illustrates a medical device 200 having a melt-pressed film 210 with a first and second diffusion barrier layer 220a, 220b, respectively. The film 210 includes a first surface, 210a, having a first diffusion barrier 220a disposed thereon, and a second surface, 210b, having a second diffusion barrier 220b disposed thereon. The melt-pressed film 210 is sandwiched between the first and second diffusion barrier layer 220a, 220b, resulting in a tri-layer structure. It should be noted that the melt-pressed film 210 extends to the edge of both the first and second diffusion barrier layers 220a, 220b. The melt-pressed film 210 comprises a copolymer composition of glycolide, trimethylene carbonate, caprolactone, and lactide in combination with bupivacaine. Both the first and second diffusion barrier layers 220a, 220b, comprise a copolymer of glycolide and ε-caprolactone.

Figure 3:
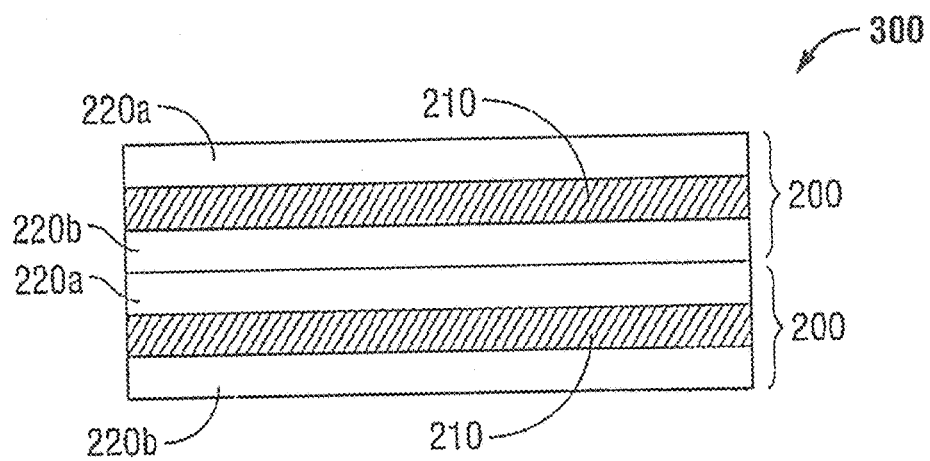
FIG. 3 illustrates a cross-sectional view of another embodiment of a medical device in accordance with the present disclosure.

FIG. 3 illustrates two tri-layer structures 200 (as shown in FIG. 2) stacked on top of each other to form a medical device 300. Each of the tri-layer structures 200 includes a first diffusion barrier film 220a, a second diffusion barrier film 220b, and melt-pressed film 210 therebetween. When stacked, medical device 300 may include increased payload of the therapeutic agent without compromising mechanical properties. It is envisioned that more than two tri-layer structures 200 may be stacked on top of each other to form the medical device. In embodiments, 2 to about 25 of the tri-layer structures 200 may be stacked on top of each other to form the medical device 300.

The tri-layer structures may be created utilized methods including but not limited to adhesives, glues, solvents (e.g., solvent welding), energy sources e.g., heat, lasers, ultrasonics, and other lamination techniques.

Figure 4:
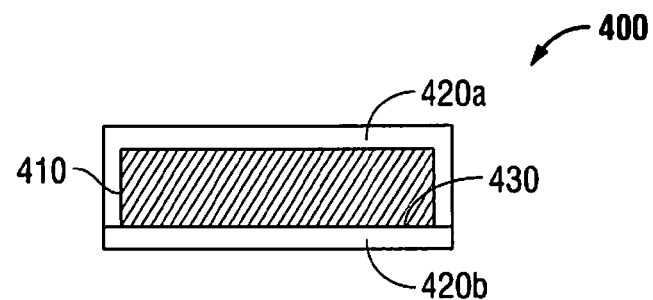
FIG. 4 illustrates a cross-sectional view of yet an another embodiment of a medical device in accordance with the present disclosure.

It will be understood that FIG. 4 is a similar embodiment to FIG. 2 and therefore will only be described with respect to the differences therebetween. The medical device 400 includes a tri-layer structure, however the melt-pressed film 410 does not extend to the outer edge 420 of the medical device 400. The melt-pressed film 410 is completely enclosed within the diffusion barrier layers. By controlling the distance of the melt-pressed film (containing a therapeutic agent) to the outer edge 420 the release of the therapeutic agent may be altered/controlled.

Figure 5A:
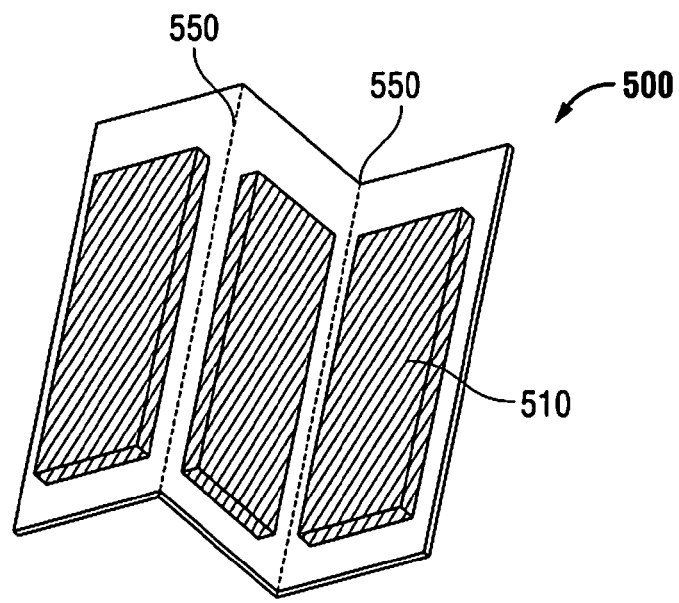
FIGS. 5A-5B illustrate a perspective view and a cross-sectional view of an alternate embodiment of a medical device in accordance with the present disclosure.
Figure 5B:
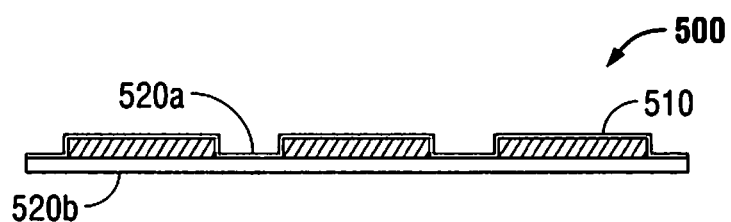

Still, in other embodiments, medical devices may have discontinuous, or a series of melt-pressed films. As shown in FIGS. 5A-5B, the medical device 500 includes a first, continuous diffusion barrier layer 520a, a second, continuous diffusion barrier layer 520b and a discontinuous melt-pressed film 510, disposed therebetween. The device 500 may be created using a template. Strips or sections of the melt-pressed film 510 may be strategically placed on the second diffusion barrier layer 520b. The first diffusion barrier layer 520a may then be sprayed thereon the films 510 and the second diffusion barrier layer 520b. The first diffusion barrier layer 520a may also seal or connect the melt-pressed film 510 to the second diffusion barrier layer 520b. As illustrated in FIG. 5A, perforations 550 enable the medical device 500 to be folded for insertion into the body cavity. The perforations 550 also enable the end user, e.g., the surgeon, to choose the size and dosing of the medical device.

Figures 6, 7:
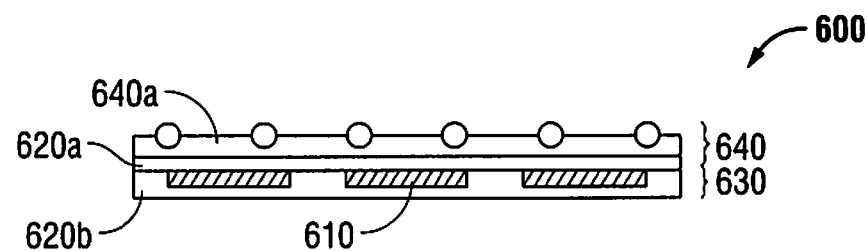
FIG. 6 illustrates a cross-sectional view of a composite medical device in accordance with the present disclosure.
FIG. 7 is a chart illustrating the various zones and associated temperatures of the twin screw extruder of FIG. 1.

In further embodiments, medical devices of the present disclosure may be further combined with meshes or other scaffolds to create a composite medical device. FIG. 6 illustrates a composite medical device in accordance with the present disclosure. The composite 600, includes collagen backed mesh 640, such as Parietex™ Composite Mesh (PCO) having a tri-layer structure 630 according to the present disclosure. The mesh 640 includes a collagen film 640a on a first surface thereof. The tri-layer medical device 630 is positioned adjacent the mesh 640. The tri-layer medical device 630 includes a first diffusion barrier layer 620a, a second diffusion barrier layer 620b, and a discontinuous melt-pressed film 610 disposed therebetween. As illustrated, the first diffusion barrier layer 620a is disposed directly on the collagen film 640a, opposite the fibers of the mesh. The melt-pressed discontinuous film 610 is positioned between the first and second diffusion barrier layers, 620a, 620b, respectively.

Methods for making composite devices include directly spraying a barrier layer onto the mesh or scaffold and creating the medical device directly onto the mesh or scaffold. For example, a first barrier layer may be sprayed onto a surface of the mesh. Next, the melt-pressed film may be placed on the first barrier layer. Finally, the second barrier layer may be applied to the melt-pressed film, creating the composite medical device. Other methods for creating composite medical devices include utilizing adhesives or glues. Alternatively, energy sources such as heat or ultrasonic energy may be used to combine, or fuse portions together to create a composite medical device.

EXAMPLE 1

To achieve a baseline, a resin comprising a copolymer of lactide, glycolide, trimethylene carbonate, and caprolactone was loaded into the hopper above Zone 1 of the screw extruder shown in FIGS. 1A-1I and described herein. The operating temperatures of the different Zones are illustrated in FIG. 7. The material properties of the extruded strand appeared similar to extruding the polymer using a single screw extruder.

Next, the copolymer of lactide, glycolide, trimethylene carbonate, and caprolactone was loaded into the hopper and bupivacaine was added at Zone 3. Five trials were run, having bupivacaine concentrations from about 0% to about 50%, the details of which are shown in FIG. 8. Subjective observation of the copolymer and bupivacaine mixture yielded a brittle extruded strand, however, the mixture withstood the processing and otherwise maintained mechanical integrity.

EXAMPLE 2

The trial compositions recovered from Example 1 were pressed into films utilizing heat press. More specifically, the compositions containing 40% and 50% of the therapeutic agent were each pressed into 14 films.

EXAMPLE 3

Figures 10, 11:
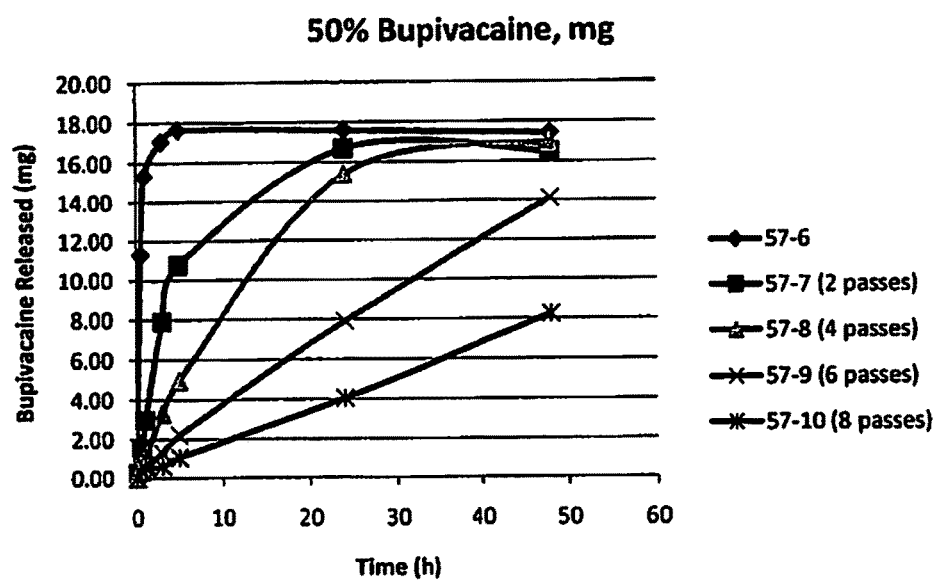
FIG. 10 is a graph illustrating bupivacaine release vs. time for another embodiment of a medical device in accordance with the present disclosure.
FIG. 11 is a graph illustrating extruding temperatures of the twin screw extruder of FIG. 1, for use with an alternate copolymer.

The melt-pressed films of Example 2 were sprayed with a solution of methylene chloride and glycolide/caprolactone utilizing ultrasonic spray coating machine. Films were coated with 2, 4, 6, and 8 passes of the solution on each side of the film. Films were dried and high permeation liquid chromatography (HLPC) was performed on the samples. Drug release vs. time of the medical devices having 40% and 50% by weight of bupivacaine is illustrated in FIGS. 9 and 10.

EXAMPLE 4

A resin comprising a copolymer of glycolide, dioxanone, and trimethylene carbonate, was loaded into the hopper above Zone 1 of the screw extruder shown in FIGS. 1A-1I and described herein. The operating temperatures of the different Zones are illustrated in FIG. 11. The material properties of the extruded strand appeared similar to extruding the polymer using a single screw extruder.

Next, the copolymer of glycolide, dioxanone, and trimethylene carbonate was loaded into the hopper and bupivacaine was added at Zone 3. The mixture of the bupivacaine and copolymer immediately degraded beyond salvage and could not withstand any drawing.

It will be understood that various modifications may be made to the embodiments disclosed herein. Therefore, the above description should not be construed as limiting, but merely as exemplifications within the scope and spirit of the claims appended hereto.

What we claim is:

1. A medical device comprising:
   a first spray coated diffusion barrier layer,
   a second spray coated diffusion barrier layer, and
   a melt-pressed film comprising a therapeutic agent disposed therebetween.

2. The medical device of claim 1, wherein the melt-pressed film comprises a material selected from the group consisting of homopolymers and copolymers of lactide; glycolide; epsilon-caprolactone, p-dioxanone; trimethylene carbonate; alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one; 1,5-dioxepan-2-one; 6,6-dimethyl- 1,4-dioxan-2-one; 2,5-diketomorpholine; pivalolactone; α, α diethylpropiolactone; ethylene carbonate; ethylene oxalate; 3-methyl-1,4-dioxane-2,5-dione; 3,3-diethyl-1,4-dioxan-2,5-dione; and 6,8-dioxabicyclooctane-7-one.

3. The medical device of claim 2, wherein the melt-pressed film comprises glycolide, trimethylene carbonate, epsilon-caprolactone, and lactide.

4. The medical device of claim 2, wherein the melt-pressed film comprises a random copolymer.

5. The medical device of claim 1, wherein at least the first or the second diffusion barrier layer comprises a biodegradable material.

6. The medical device of claim 1, wherein at least the first or second diffusion barrier layer comprises glycolide and caprolactone.

7. The medical device of claim 1, wherein at least the first diffusion barrier layer or the second diffusion barrier layer is from about 1 micron to about 50 microns thick.

8. The medical device of claim 1, wherein the melt-pressed film is from about 1 millimeter to about 10 millimeters thick.

9. The medical device of claim 1, wherein the therapeutic agent is selected from the group consisting of anti-adhesives, antimicrobials, analgesics, and, anesthetics.

10. The medical device of claim 1, wherein the therapeutic agent is bupivacaine.

11. The medical device of claim 10, wherein the therapeutic agent is at a concentration of from about 30% to about 50% of the melt-pressed film.

12. A medical device comprising:
   a copolymer film including about 69% glycolide, about 7% trimethylene carbonate, about 17% caprolactone, about 7% lactide;
   wherein the copolymer film is disposed between a first and second barrier layer; and,
   at least one of the first and second barrier layers includes about 90% caprolactone and about 10% glycolide.

13. The medical device according to claim 12, wherein the copolymer film includes a therapeutic agent at a concentration of from about 40% by weight to about 50% by weight.

* * * * *